United States Patent
Neame

(10) Patent No.: US 8,419,075 B2
(45) Date of Patent: Apr. 16, 2013

(54) TUBES AND THEIR MANUFACTURE

(75) Inventor: Simon Neame, Kent (GB)

(73) Assignee: Smiths Group PLC, London (GB)

( * ) Notice: Subject to any disclaimer, the term of this patent is extended or adjusted under 35 U.S.C. 154(b) by 358 days.

(21) Appl. No.: 12/734,962

(22) PCT Filed: Nov. 12, 2008

(86) PCT No.: PCT/GB2008/004077
§ 371 (c)(1),
(2), (4) Date: Jun. 4, 2010

(87) PCT Pub. No.: WO2009/087347
PCT Pub. Date: Jul. 16, 2009

(65) Prior Publication Data
US 2010/0244432 A1    Sep. 30, 2010

(30) Foreign Application Priority Data

Jan. 4, 2008   (GB) .................................... 0800112.5

(51) Int. Cl.
*F16L 47/00*    (2006.01)

(52) U.S. Cl.
USPC .................. 285/290.3; 285/292.1; 285/293.1; 264/262; 604/905

(58) Field of Classification Search .............. 285/285.1, 285/286.1, 290.3, 292.1, 293.1, 21.2, 21.3, 285/290.2, 21.1, 235; 264/251, 248, 262, 264/259; 604/905
See application file for complete search history.

(56) References Cited

U.S. PATENT DOCUMENTS

| | | | | |
|---|---|---|---|---|
| 46,395 A * | 2/1865 | Scaife | ........................ | 285/293.1 |
| 429,947 A * | 6/1890 | Nichols | ...................... | 285/290.3 |
| 539,112 A * | 5/1895 | Barrett | ........................ | 285/285.1 |
| 2,211,776 A * | 8/1940 | Haury | ........................... | 285/231 |
| 2,246,404 A * | 6/1941 | Ross | ........................... | 285/293.1 |
| 2,845,657 A * | 8/1958 | Beare | ............................ | 264/262 |
| 3,400,951 A * | 9/1968 | Jacobson | .................. | 285/293.1 |
| 3,936,078 A * | 2/1976 | Wallyn | ....................... | 285/294.1 |
| 4,552,384 A * | 11/1985 | Cyriax | ........................ | 285/293.1 |
| 4,682,797 A * | 7/1987 | Hildner | ........................ | 285/21.2 |
| 5,316,350 A | 5/1994 | Kollenbrandt et al. | | |
| 5,333,650 A * | 8/1994 | Folkman | .................... | 285/286.2 |
| 5,406,983 A * | 4/1995 | Chambers et al. | ......... | 285/294.1 |
| 6,070,915 A * | 6/2000 | Luo | ............................. | 285/286.2 |
| 6,099,975 A * | 8/2000 | Peterson et al. | ............. | 264/241 |
| 6,808,209 B2 * | 10/2004 | Nakaya et al. | ............... | 285/21.1 |
| 7,988,204 B2 * | 8/2011 | Lewis et al. | ................. | 285/286.1 |
| 8,071,003 B2 * | 12/2011 | Imaeda | ......................... | 264/262 |
| 8,172,275 B2 * | 5/2012 | Sumrall et al. | ............. | 285/286.1 |

FOREIGN PATENT DOCUMENTS

JP          52024318 A  *  2/1977

* cited by examiner

*Primary Examiner* — David E Bochna
(74) *Attorney, Agent, or Firm* — Louis Woo

(57) ABSTRACT

An end fitting (31) is formed at the patient end of an inner cannula (3) for a tracheostomy tube (1) by punching small holes (33) close to one end (34) of an ePTFE shaft (30). The end is then swaged to form an expanded region (30') and a preformed tubular insert (40) of a thermoplastic material is inserted to cover the holes (33) on the inside. An outer part (46) of the same thermoplastic material is then overmolded on the outside of the shaft 30 so that its material (47) flows through the holes (33) and bonds with the inner insert (40), thereby securing the inner and outer parts together around the end of the shaft.

16 Claims, 2 Drawing Sheets

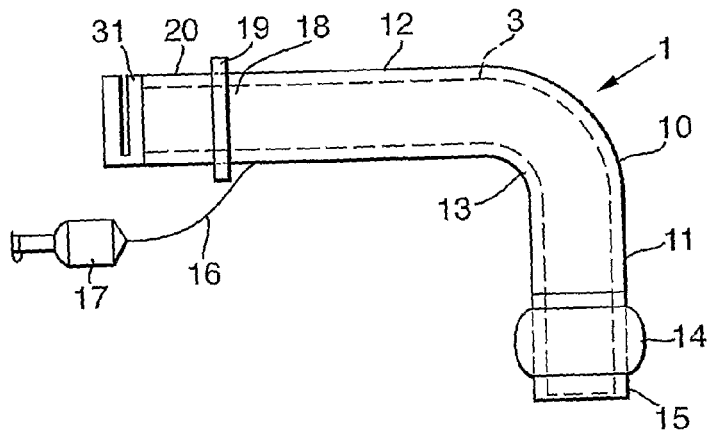
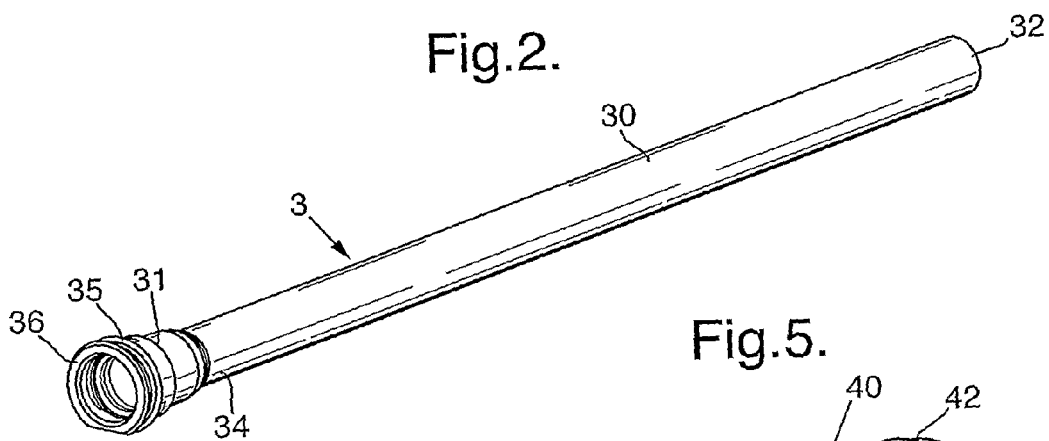
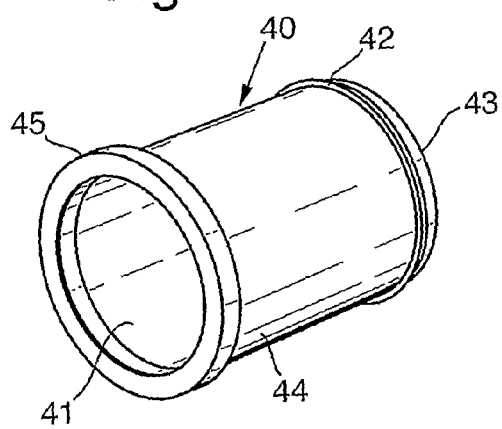
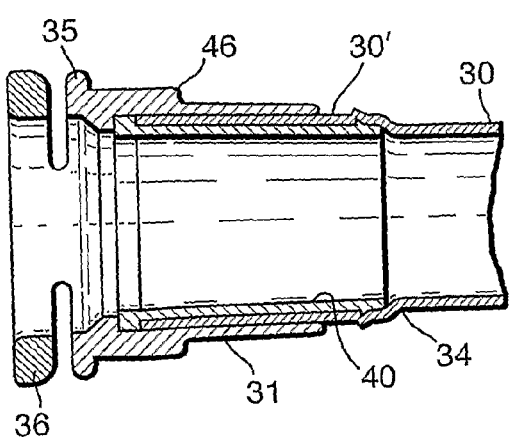

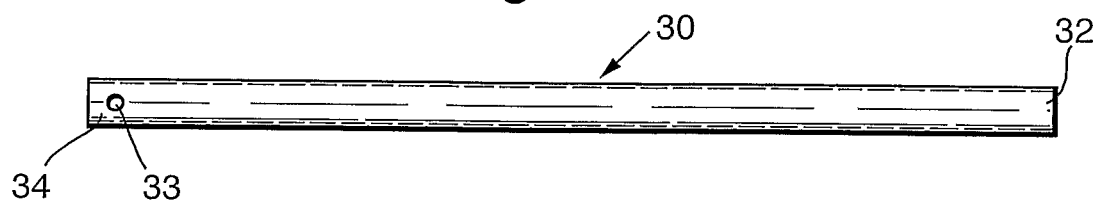
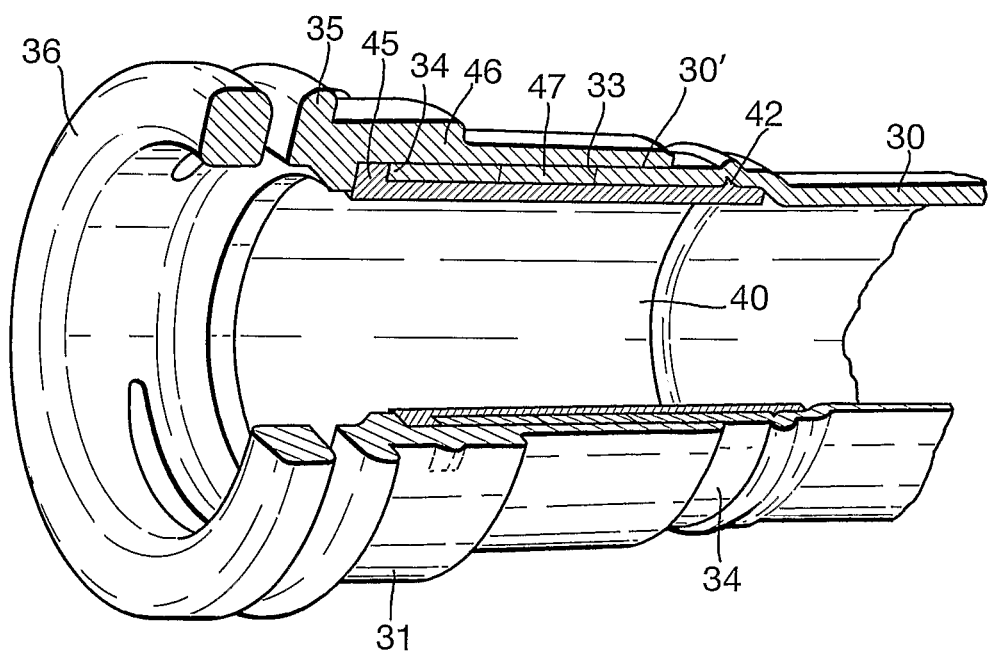

TUBES AND THEIR MANUFACTURE

FIELD OF INVENTION

This invention relates to tubes of the kind having a shaft and an end fitting attached with the shaft at one end.

BACKGROUND OF INVENTION

Tubes are used in many medical and non-medical applications. For example, tracheostomy tube assemblies commonly include an outer tube and an inner tube or cannula that is a removable fit within the outer tube. The inner tube can be removed and replaced periodically to ensure that the passage through the assembly does not become blocked by secretions. This avoids the need frequently to remove the outer tube.

The inner tube presents various problems because it must be thin walled and a close fit within the outer tube so as to limit the resistance to flow of gas along the assembly. It must, however, also be sufficiently stiff to be inserted in the outer tube without buckling or kinking. A particularly suitable material for the inner cannula is PTFE or expanded PTFE (ePTFE). The use of such a material in an inner cannula is described in WO94/01156 and in WO2004/101048. The Flextra tube sold by Tyco Healthcare is made of ePTFE. Whilst such a material has various advantages, the material makes it difficult to attach a hub or end fitting to the machine end of the shaft of the cannula securely in a reliable and low cost manner. There are also other tubes where it can be difficult to attach an end fitting.

It is an object of the present invention to provide an alternative tube and a method of its manufacture.

BRIEF SUMMARY OF INVENTION

According to one aspect of the present invention there is provided a tube of the above-specified kind, characterised in that the shaft has an opening formed through the wall of the shaft close to the one end, that a cylindrical inner component extends over the inside of the opening within the one end, that a separate outer component extends over the outside of the opening on the outside of the shaft, and that material extends between the outer and inner components through the opening so that the outer component is bonded to the inner component via the opening.

The material extending between the outer and inner components is preferably material of the outer or inner component flowed through the opening. The outer component is preferably overmoulded onto the one end. The inner and outer components are preferably of a thermoplastic material. The shaft is preferably of a PTFE material, such as ePTFE. The shaft may be swaged to form an expanded region at the one end in which the cylindrical inner component is inserted. The tube may be an inner tube of a tracheostomy tube assembly.

According to another aspect of the present invention there is provided an assembly of an outer tracheostomy tube and an inner tube according to any one of the preceding claims.

According to a further aspect of the present invention there is provided a method of manufacture of a tube including the steps of providing a tubular shaft, forming an opening through the wall of the shaft close to one end, providing separate inner and outer tubular components extending over the opening respectively on the inside and outside of the shaft, and causing material to extend through the opening between the inner and outer tubular components to bond them with one another.

According to a fourth aspect of the present invention there is provided a method of manufacture of a tube including the steps of providing a tubular shaft, forming an opening through the wall of the shaft close to one end, inserting an tubular inner component in the one end of the shaft to cover the inner end of the opening, and moulding over the outside of the one end of the shaft a tubular outer component so that the material of the outer part flows through the opening and bonds with the inner component.

The material of the shaft is preferably different from that of the inner and outer parts. The shaft is preferably of a PTFE material and the inner and outer tubular parts are preferably of the same thermoplastic material.

BRIEF DESCRIPTION OF THE DRAWINGS

A tracheostomy assembly with an inner cannula and its method of manufacture according to the present invention, will now be described, by way of example, with reference to the accompanying drawings, in which:

FIG. 1 shows the assembly schematically;

FIG. 2 is a perspective view of the inner cannula;

FIG. 3 is a cross-sectional side elevation view of the machine end of the inner cannula to an enlarged scale;

FIG. 4 is a side elevation view of the shaft of the inner cannula before swaging and attachment of the end fitting;

FIG. 5 is a perspective view of an insert used to form the end fitting of the inner cannula; and FIG. 6 is a partly cut-away perspective view of the end fitting on the machine end of the inner cannula.

DETAILED DESCRIPTION OF INVENTION

With reference first to FIG. 1, the tracheostomy tube assembly comprises an outer tube 1 and an inner tube or cannula 3, which is removable from the outer tube so that it can be periodically replaced in the usual way.

The outer tube 1 is entirely conventional having a shaft 10 with straight forward or patient end section 11 and rear or machine end section 12 joined by a right-angle bend section 13. Alternative outer tubes could be smoothly curved along their entire length or could be highly flexible and reinforced with a natural straight shape. A sealing cuff 14 embraces the shaft 10 close to its patient end 15; this can be inflated for sealing, or deflated for insertion and removal, via an inflation line 16 and a combined inflation indicator balloon and coupling 17. At its rear end 18, the outer tube 1 has a flange 19 to which a tape (not shown) can be attached for securing the assembly around the neck of the patient. A hub 20 projects from the machine side of the flange 19 by which gas connection can be made to the tube 1. In use, the tube 1 extends through a surgically-made tracheostomy opening in the neck, with the patient end 15 of the tube 1 located in the trachea. The cuff 14 is inflated to form a seal between the outside of the tube and the tracheal wall so that gas flow is confined along the bore of the tube. The machine end 18 of the tube 1 extends externally of the tracheostomy.

With reference now also to FIGS. 2 to 4, the inner tube or cannula 3 comprises a shaft 30 and a machine end fitting 31. The inner cannula 3 is about 194 mm long and its shaft 30 has an internal diameter of about 8 mm with an external diameter of about 9 mm along the major part of its length. In use, the cannula 3 extends as a close sliding fit within the bore of the outer tube 1 with the patient end 32 of the cannula extending substantially level with the patient end 15 of the outer tube and with its end fitting 31 locating in the hub 20 of the outer tube.

The shaft 30 is of ePTFE and is made by cutting from a length of extruded stock tubing. The nature of the shaft 30 is that it can flex readily to conform to the shape of the outer tube 1 without kinking as it is inserted. The shaft material has a very low coefficient of friction so that it can be inserted readily into the outer tube 1 as a close sliding fit without excessive axial compression forces being produced of a kind that could cause the shaft 30 to buckle. Two circular openings or holes 33 with a diameter of about 3 mm are punched through the wall of the shaft 30 diametrically opposite one another at a location spaced 5 mm from the machine end 34 of the shaft. The purpose of these openings 33 will become apparent later. The rear or machine end of the shaft 30 including the holes 33 is then swaged outwardly to form an expanded region 30'.

The machine end fitting 31 on the inner cannula 3 is made of a material different from that of the shaft 30 and, in particular, it is made of a flowable thermoplastic material such as low density polyethylene (LDPE), which has a low melt temperature. Other thermoplastic materials could be used such as a polyolefin or polyurethane. Externally, the end fitting 31 has a stepped profile to conform to the inner surface of the hub 20 on the outer tube 1 within which it is fitted. An enlarged flange 35 projects outwardly towards the rear end of the fitting 31, its size being selected so that it abuts the rear end of the hub 20 and limits the extent of insertion of the inner cannula 3. The end fitting 31 is also provided with a hinged ring-pull feature 36 of the kind described in U.S. Pat. No. 4,817,598 to facilitate removal of the inner cannula. The LDPE used to make the fitting 41 is particularly suitable for forming the flexible hinge in the ring-pull feature 36.

The materials of the machine end fitting 31 and the shaft 30 do not enable them to be bonded together in a reliable manner so they are instead attached with one another by a mechanical arrangement. Briefly, the machine end fitting 31 is formed by a preformed insert attached with an overmoulded outer component. The insert or inner component 40 is shown in FIG. 5 and is a preformed cylindrical component moulded from LDPE and is about 12.5 mm long, which is approximately equal to the length of the expanded region 30' of the shaft 30. The insert 40 has a circular section with a smooth, uninterrupted inner surface or bore 41 and tapers at an angle of about 2.5° to an enlarged diameter rearwardly. Externally, the insert 40 is also tapered and is formed with an annular, rearwardly inclined tooth or barb 42 close to its forward end 43. At its rear end 44 the insert 40 has an externally-projecting flange 45. The external diameter of the insert 40 at its forward end 43 is equal to the internal diameter of the swaged region 30' of the shaft 30 so that the insert can be pushed into the end of the shaft. The internal diameter of the insert 40 is the same as that of the main part of the shaft 30 so that the bore through the insert and shaft is smooth and continuous. The insert 40 is pushed fully into the expanded region 30' until the flange 45 abuts the rear end 34 of the shaft 30. When fully inserted the insert 40 extends over the inner surface of the two openings 33 in the shaft 30. The barb 42 improves retention of the insert 40 in the shaft. The insert could have more than one barb and the barb or barbs need not be annular but could be separate barbs spaced around the insert.

The end fitting 31 is completed by inserting the rear end 34 of the shaft 30 and insert 40 into a mould (not shown) and overmoulding an outer tubular member or component 46 onto the shaft 30 as most clearly shown in FIG. 6. This outer part 46 extends from a location just rearwardly of the barb 42 on the insert 40 and forwardly of the openings 33 in the shaft 30 so that the outer end of these are both covered by the outer part. Externally, the outer component 46 defines the external shape of the end fitting 31 with its ring-pull feature 36. The outer component 46 is moulded over the outer curved surface and the rear end surface of the flange 45 and thereby bonds with the flange and traps it between the outer part and the shaft 30. Material 47 of the overmoulded outer part 46 also flows into the two openings 33 in the shaft 30 during the moulding operation and bonds with the outer surface of the insert 40 exposed by the openings. It will be appreciated that, when the material 47 of the overmoulded outer component 46 has hardened, the outer component will be intimately and securely bonded with the insert 40 both at the flange 45 and through the openings 33. This securely locks the shaft 30 with the end fitting 31 without the need for any bond between the two different materials. Because the inner cannula is preformed, it helps support the shaft during this overmoulding operation.

The invention is not confined to inner cannulae but could be used with other tubes for medical or non-medical applications and is especially advantageous where the tube shaft is of a material that does not bond readily with the end fitting. Although preferably two openings are provided through the shaft wall, the invention is applicable with only one opening or with more than two. Instead of using a preformed inner component and overmoulding externally, the end fitting could be provided by a preformed outer component and by moulding the inner component. Instead of bonding the inner and outer components with one another by material of one or other of these components a different material could be used to form the bonds. For example, the end fitting could be provided by preformed inner and outer components and an adhesive added to the openings to bond the two components with one another.

The invention claimed is:

1. A tube having a shaft and an end fitting attached with the shaft at one end, characterized in that the shaft has an opening formed through the wall of the shaft close to the one end, that a cylindrical inner component separate from the shaft extends over the inside of the opening within the one end, that an outer component separate from the shaft and the inner component extends over the outside of the opening on the outside of the shaft, and that material extends between the outer and inner components through the opening so that the outer component is bonded to the inner component via the opening and the end fitting provided by the inner and outer components is interlocked with the shaft by the material extending through the opening.

2. A tube according to claim 1, characterized in that the material extending between the outer and inner components is material of the outer and inner component flowed through the opening.

3. A tube according to claim 1, characterized in that the outer component is overmolded onto the one end.

4. A tube according to claim 1, characterized in that the inner and outer components are of a thermoplastic material.

5. A tube according to claim 1, characterized in that the shaft is of PTFE material.

6. A tube according to claim 5, characterized in that the shaft is of a ePTFE.

7. A tube according to claim 1, characterized in that the shaft is swaged to form an expanded region at the one end in which the cylindrical inner component is inserted.

8. An assembly of an outer tracheostomy tube and an inner tube having a shaft and an end fitting attached with the shaft at one end, characterized in that the shaft has an opening formed through the wall of the shaft close to the one end, that a cylindrical inner component extends over the inside of the opening within the one end, that a separate outer component extends over the outside of the opening on the outside of the shaft, and that material extends between the outer and inner components through the opening so that the outer component is bonded to the inner component via the opening.

9. A method of manufacture of a tube including the steps of providing a tubular shaft, forming an opening through the wall of the shaft close to one end, providing inner and outer tubular components separate from one another and from the shaft extending over the opening respectively on the inside and outside of the shaft, and causing material to extend through the opening between the inner and outer tubular components to bond them with one another and to interlock the inner and outer components with the shaft by the material extending through the opening.

10. A method according to claim 9, characterized in that the material of the shaft is different from that of the inner and outer parts.

11. A method according to claim 9, characterized in that the shaft is of a PTFE and the inner and outer parts are of the same thermoplastic material.

12. A tube made by a method according to claim 9.

13. A method of manufacture of a tube including the steps of providing a tubular shaft, forming an opening through the wall of the shaft close to one end, inserting a preformed tubular inner component in the one end of the shaft to cover the inner end of the opening, and molding over the outside of the one end of the shaft a tubular outer component so that the material of the outer component flows through the opening and bonds with the inner component thereby interlocking the inner and outer components with the shaft by the material flowed through the opening.

14. A method according to claim 13, characterized in that the material of the shaft is different from that of the inner and outer parts.

15. A method according to claim 13, characterized in that the shaft is of a PTFE and the inner and outer parts are of the same thermoplastic material.

16. A tube made by a method according to claim 13.

* * * * *